United States Patent [19]

Marchioni et al.

[11] Patent Number: 4,624,101
[45] Date of Patent: Nov. 25, 1986

[54] PROCESS AND COMPOSITION FOR PREVENTING THE DISCOLORATION OF RADIATION STERILIZED CELLULOSIC MATERIAL EXPOSED TO ELEVATED POST-STERILIZATION TEMPERATURES

[75] Inventors: Bruce C. Marchioni; Dan Posey, both of El Paso, Tex.

[73] Assignee: American Hospital Supply Corporation, Evanston, Ill.

[21] Appl. No.: 613,280

[22] Filed: May 24, 1984

[51] Int. Cl.$^4$ ................................................ A61L 2/08
[52] U.S. Cl. ...................................... 53/425; 128/155; 206/438; 206/440; 206/524.4; 422/22; 428/74; 428/532
[58] Field of Search .............................. 422/21, 22, 24; 128/155; 206/438, 440; 428/74, 532; 53/425

[56] References Cited

U.S. PATENT DOCUMENTS 3,494,722 2/1970 Grey .

FOREIGN PATENT DOCUMENTS 499331 1/1954 Canada .
942374 11/1963 United Kingdom .................. 422/21

OTHER PUBLICATIONS

Boucher, "Advances in Sterilization Techniques", American Journal of Hospital Pharmacy, 29:660–672, Aug. 1972.

Morganstern, "The Future of Radiation Sterilization", 1978.
"Radiation Sterilized Cotton Surgical Sutures", *American Drystuff Reporter,* vol. 53, No. 23, pp. 33–34 (Nov. 9, 1964) by Florine A. Blouin and Jett C. Arthur, Jr.
W. C. Bradbury, "Physical and Chemical Effects of Ionizing Irradiation on Cellulosic Material", *Technical Developments and Prospects of Sterilization Ionizing Radiation,* Minutes of the International Conference in Vienna, Apr. 1–4, 19740, Multi-Science Publication, Ltd., Montreal, Canada.
F. Antoni, "The Effect of Ionizing Radiation on Some Molecules of Biological Importance", Institute of Medical Chemistry, Semmelweis University of Medicine, Budapest, Hungary.

*Primary Examiner*—Barry S. Richman
*Assistant Examiner*—William R. Johnson
*Attorney, Agent, or Firm*—Leydig, Voit & Mayer

[57] ABSTRACT

Sterilized cellulosic material which resists discoloration when exposed to undue post-sterilization heating (e.g., 100° F. to 150° F.) is provided by stabilizing the water content by weight of the pre-sterilized cellulosic material to not less than 6.5% by weight—preferably, at least about 8% by weight—with the water content being maintained at less than about 12% by weight, preferably less than about 10%, so that the cellulosic material remains dry to the touch.

13 Claims, No Drawings

PROCESS AND COMPOSITION FOR PREVENTING THE DISCOLORATION OF RADIATION STERILIZED CELLULOSIC MATERIAL EXPOSED TO ELEVATED POST-STERILIZATION TEMPERATURES

TECHNICAL FIELD OF THE INVENTION

The invention generally relates to the discoloration of sterilized cellulosic material and, more particularly, to a process and composition for reducing post-treatment discoloration of cellulosic material sterilized by irradiation.

BACKGROUND OF THE INVENTION

For a variety of medical applications and the like, cellulosic materials such as, for example, cotton gauze are employed. Such materials must be sterilized; and, as is well known, adequate sterilization of such cellulosic materials can be accomplished by either (1) exposure to radiation dosage levels sufficient to cause biological death or (2) treatment with chemicals such as ethylene oxide. Although sterilization by radiation is often considered preferable to sterilizing cellulosic material by chemical treatment, particularly where large volume products are involved, cellulosic products (e.g., cotton gauze) often discolor during radiation sterilization. Thus, although completely sterilized, the product has an unclean cosmetic appearance and, therefore, is commercially undesirable. It is believed that one of the causes of the discoloration is the formation of free radicals (e.g., lower molecular weight polysaccharides) in the cellulosic material which gives the material a yellow appearance. Although the presence of the free radicals does not affect the sterility of the cellulosic material, its coloring of the material often affects the consumer's opinion of the quality or cleanliness of the product which it comprises.

Whatever the reason for the discoloration, it is known that discoloration which might otherwise occur during the sterilizing irradiation of cellulosic material can be prevented by controlling the water content of the cellulosic material during such irradiation. For example, in the Minutes of the International Conference in Vienna, Apr. 1–4, 1974 published by Multiscience Publication, Ltd., Montreal, Canada and entitled "Technical Developments and Prospects of Sterilization Ionizing Radiation", an article by W. C. Bradbury entitled "Physical and Chemical Effects of Ionizing Irradiation on Cellulosic Material" reports that at a water content by weight greater than 6% it is difficult to visually distinguish irradiated cellulosic material from untreated cellulosic material. It is also known that controlling the radiation dosage can reduce the radiation-induced discoloration of the cellulosic material.

Nevertheless, and despite some minimization of the problem by suitable adjustment of the radiation conditions employed during sterilization, the yellowing problem discussed herein remains. More particularly, it has been observed that, in some fashion, storage and handling seem to exacerbate the problem. As far as has been ascertained, prior work in this field has not even adequately exposed the principal causes of this problem, much less how such causes can be satisfactorily minimized or even eliminated.

SUMMARY OF THE INVENTION

It is accordingly a primary object of the present invention to provide a process for improving the color stability of post-sterilized cellulosic material. In this connection, it is a related object of this invention to provide a process for improving the color stability of cellulosic material which has been sterilized by radiation, without altering the touch or look of the material.

A further object of this invention is to increase the resistance of cellulosic material to post-sterilization discoloration during storage, transportation and the like.

Yet another object of this invention is to provide sterilized cellulosic material which maintains an antiseptic appearance even after long storage and/or transporting time periods.

Other objects and advantages of the invention will become apparent from the following detailed description.

The present invention is, in part, predicated on the discovery that a principal cause of post-sterilization discoloration is exposure to relatively high temperatures, even for relatively short periods of time. It was thus found that exposure to temperatures in the range of 100° F. to 150° F. was a principal cause of yellowing. Such conditions can often occur, particularly during transportation and/or storage in the warmer climates or in the summer months in many areas of the country.

This invention is likewise predicated in part on the discovery that discoloration due to undue thermal exposure can be adequately minimized by maintaining the water content within relatively close limits during sterilization. More specifically, it has been found that maintaining the water content of the cellulosic material at a level greater than about 6% by weight of the cellulosic material during irradiation sterilization will adequately minimize discoloration that would otherwise occur upon exposure to extreme thermal conditions following irradiation. More preferably, the water content is maintained at a level of at least about 8% by weight of the cellulosic material. Increased water levels do not appear to provide any further benefits of significance, and, indeed, may prove detrimental. Thus, at relatively high water contents, the cellulosic material may be perceived as having a damp or clammy feeling. It is, accordingly, preferred to maintain a water level such that the cellulosic material remains dry to the touch. The maximum water content suitable can be readily determined. It has been found that a post-irradiation water content of about 10 percent by weight or so can be tolerated.

Although it is not intended that the invention be limited to a particular theory of operation, it is believed that post-sterilization exposure to undue thermal conditions encourages the increased concentration of free radicals in the cellulosic material which, in turn, is believed to be associated with the post-sterilization discoloration of the cellulosic material. It is hypothesized that the addition of more than 6% water by weight of the material provides sufficient hydrogen ions (after irradiation) to absorb the heat-generated free radicals and thereby stabilize the cellulosic material's color.

DETAILED DESCRIPTION OF THE PREFERRED EMBODIMENT

In accordance with one important aspect of the invention, sterilized cellulosic material contained in vapor impermeable packaging is stabilized by maintaining the water content at a suitable level during sterilization which will, in turn, prevent noticeable discoloration of the material upon subsequent exposure to high temperatures in the range of 100° F. to 150° F. To this end, the water content of the material is adjusted to provide a pre-sterilization water content of at least 6 percent by weight of the cellulosic material. Stated from the functional standpoint, the water content should be maintained at a level during sterilization such that the post-sterilization exposure to undue thermal conditions (i.e., temperatures in the range of 100° F. to 150° F.) will not result in yellowing to the degree that such yellowing is visually detectable; yet, the water content should not be so excessive that, after irradiation, the material is damp to the touch. It should be appreciated that irradiation of the cellulosic material may reduce the water content of the packaged cellulosic material somewhat, viz.—on the order of perhaps 1 to 2% by weight. It may accordingly be desirable to take this into account when selecting the water content utilized in the pre-humidification step. Unless indicated otherwise, all the percentage water contents for the cellulosic material mentioned hereinafter refer to pre-irradiation values.

A water content by weight of at least 8% insures the color stability of the cellulosic material during irradiation and subsequent exposure to temperatures as high as 150° F. during storage, transportation and the like. A water content by weight of less than 8% but greater than 6% may also provide satisfactory results depending on the degree of post-irradiation heating to which the cellulosic material is exposed. Restricting the water content to less than approximately 12%, preferably less than 10%, has been found necessary to maintain the tactile dryness of the cellulosic material.

It will be appreciated by those skilled in the art that various mechanisms and processes may be utilized to prehumidify the cellulosic material and to stabilize its content at the appropriate levels as discussed herein. For example, water may be added to the material by conditioning it at an appropriate temperature and relative humidity. Alternatively, methods such as steam injection or water spray may be suitably used. The particular method of choice may depend on variables such as product geometry, time and volume requirements, capital equipment costs, floor space limitations, degree of automation and other manufacturing limitations. As used herein, the terminology "prehumidifying" and the like is intended to mean water addition by whatever technique employed.

As an illustrative and preferred example, a cellulosic material such as cotton gauge may be prehumidified by exposure to air at a 70° F.±2° F. temperature and approximately 80% relative humidity. Exposure for a period of about 6 to 12 hours should provide adequate equilibration of the water content at about 8% by weight. Of course, whatever time period is needed to effect the equilibration should be employed. Suitable adjustment of the relative humidity and temperature will allow achievement of the specific water content desired for the particular application.

Once the cellulosic material has been conditioned to provide the requisite water content, it should be placed in a relatively water vapor impermeable packaging. Suitable materials are well known, and the particular material used is not critical. As an illustrative example, the conventionally used material for medical applications, identified as "peel pouches", have been found to be satisfactory. Thereafter, the particular cellulosic material may be irradiated, stored and/or transported in the conventional manner for the particular application. No readjustment of the water content is needed; the typically handled materials will thus be satisfactorily insulated from the yellowing effects that would otherwise occur upon exposure to undue thermal conditions.

The dosages required to adequately sterilize cellulosic materials are well known and may be employed. The appropriate minimum radiation dosage will, in large part, be dictated by the initial bioburden of the cellulosic material being sterilized, as well as by the desired level of sterility. It has been found that increasing the dosage level tends to increase the yellowing which can occur during sterilization so that it will generally be preferred to use the minimum dosage (MSD) dictated by the relative bioburden and degree of sterilization required for the particular application.

Conceptually, chemical additives other than water might be added to cellulosic materials to minimize post-sterilization discoloration caused by exposure to high temperatures. These may include compounds such as antioxidants, radiation stabilizers, and others. While these compounds may provide color stability, they may also contribute to undesirable toxicity and excessive cost. Water is accordingly the preferred additive.

The following Examples are illustrative of, and not in limitation of, the present invention. These Examples describe the preparation of sterilized cotton gauze laparotomy sponges according to the invention and the reduced discoloration of the sponges resulting from exposure to post-sterilization heating.

EXAMPLE I

This Example illustrates the effect of the water content of a cellulosic material on the discoloration of the material upon exposure to various temperatures following sterilization.

Unsterile cotton gauze laporotomy sponges were conditioned for 24 hours at specified relative humidities and then sequentially packaged, irradiated and heated for 24 hours. To package the conditioned sponges, groups of five sponges were collected and sealed in packages having low vapor permeability. In particular, the conditioned sponges were packaged in "peel pouches", one example of which is the PP1581 (part code) manufactured by Tower Products of American Hospital Supply Corporation, Evanston, Ill. 60201.

In order to measure the degree of discoloration in the sponges, ten sponges from a particular combination of relative humidity, radiation dosage and post-sterilization heating were soaked in 2.5 liters of 0.9% saline solution for 30 seconds and passed through a wringer to extract the fluid. To remove cotton fibers from the saline extract, the extract was passed through a 0.45 micron filter. The extract's relative absorbance was measured at 400 nm in a 10-cm path length cuvette against a 0.9% saline solution reference. These steps were repeated for groups of 10 sponges at various combinations of relative humidity, radiation dosage and post-sterilization heating.

A 0.9 saline solution extract of the sponges was chosen to measure the discoloration effects of post-sterilization heating since, when used commercially, the discoloration effect is usually noticed when the sponges are introduced into a physiological saline solution. Specifically, the extract from the sponges caused the physiological saline solution to turn yellow thereby unfavorably influencing the user's opinion as to the cleanliness of the sponge.

At relative humidity levels of 50%, 75% or 100% at 70°±2° F., the cotton sponges contained 3.5%, 6.5% or 10% water by weight, respectively. The sponges were irradiated with 5.5 megarads of gamma radiation and exposed to post-sterilization heating of 70° F., 100° F. or 150° F. It was found that post-sterilization discoloration of the sponges caused by exposure to heat was significantly reduced for sponges with a water content level of 6.5% or 10%. Specifically, it was found that for sponges with 10% water by weight, the extract's relative absorbance was less than 0.15 absorbance units for post-sterilization temperatures as high as 150° F. For sponges at 6.5% water content by weight, the extract showed a relative absorbance slightly greater than 0.15 only for sponges exposed to a post-sterilization temperature of 150° F.

As a target discoloration limit, 0.15 absorbance units is a virtually unperceptible discoloration to the human eye. Therefore, the test results indicated a moisture content greater than 6.5% by weight gave the sponges color stability which prevented discoloration when the sponges were exposed to post-sterilization heating. Interpolation of the test results between 6.5% water content by weight and 10% water content by weight indicates that by increasing to 8% the sponge's percentage water content by weight, the discoloration of a 0.9% saline solution extract from the sponges will remain below the target limit of 0.15 absorbance units for all the measured temperatures.

EXAMPLE II

This Example evaluates the discoloration effects caused by time delays between (1) the water content pre-conditioning of the cellulosic material and its subsequent sterilization and (2) the sterilization of the cellulosic material and its subseqeunt exposure to various temperatures.

Eight boxes of sponges were irradiated at different time intervals following preparation of the sponges in accordance with the invention. To determine any adverse effect of post-sterilization storage of the boxes on discoloration of the sponges, discoloration measurements of saline extracts from the sponges were taken at different time intervals following irradiation and exposure of the sponges to elevated temperatures.

Prior to packaging the sponges, they were placed in a conditioning room for 24 hours. In order to establish a moisture content by weight of the sponges within the region of 6% to 10%, the conditioning room was controlled at 70° F. and 90% relative humidity.

To package the conditioned sponges, groups of 5 sponges were collected and sealed in "peel pouches" of the same type as used in connection with Example I. Thirty of these packages were then placed in a cardboard box having a lining of low vapor permeability. The lining was clipped shut and the boxes were closed and taped. These packaging steps were repeated for eight boxes. This particular packaging protocol was utilized since it closely follows that used for commercial cotton gauze laporatomy sponges.

A first pair of boxes containing the sponges (boxes 1 and 2) was irradiated immediately after packaging. A second pair of boxes (boxes 3 and 4) was irradiated one week after packaging. A third pair of boxes (boxes 5 and 6) was irradiated two weeks after packaging. One box (box 7) was irradiated four weeks after packaging. In order to provide a control group, the last box of sponges (box 8) was not irradiated.

After the seven boxes were irradiated, selected numbers of the sponges were removed from the boxes at four consecutive one-week intervals measured from the time of irradiation. At each interval, the selected sponges were exposed to elevated temperatures of 70° F., 100° F. or 150° F. for a 24-hour period.

Immediately thereafter, the sponges were measured for discoloration by measuring the absorbance of a 0.9% saline solution extract in accordance with the protocol set out in Example 1. Specifically, for each pair of boxes (i.e., boxes 1 and 2, boxes 3 and 4 and boxes 5 and 6), one package of sponges (5 sponges) was removed from each box. The two packages (one from each box) were opened and the ten sponges were exposed to 70° F. for a 24-hour period; afterward, the absorbance of a 0.9% saline solution extract from the ten sponges was measured. Another package was removed from each of the boxes and the ten sponges were exposed to 100° F. for 24 hours. As before, their discoloration was measured from a 0.9% saline solution extract. This procedure was again repeated for a heat exposure of 150° F.

Since box 7 was irradiated alone, three sets of two packages of sponges (three groups of 10 sponges) were removed from the box at the end of the first, second and third week after irradiation in order to measure the absorbance of the saline extract at 70° F., 100° F. and 150° F. Similarly, for box 8—the control group of sponges—three sets of two packages of sponges were removed at the first and fourth time intervals and the absorbance of the saline extract was measured for 70° F., 100° F. and 150° F. The percentage of water content by weight, the radiation dosage and the absorbance of the saline extract for each temperature and interval are set out in Table 1.

TABLE I

| BOX NO. | TIME ELAPSED BETWEEN CONDITIONING OF SPONGES & STERILIZATION BY IRRADIATION | MOISTURE CONTENT AT TIME OF IRRADIATION | DOSE LEVEL OF IRRADIATION | ABSORBANCE OF SALINE FIRST WEEK AFTER IRRADIATION | ABSORBANCE OF SALINE SECOND WEEK OF IRRADIATION | ABSORBANCE OF SALINE THIRD WEEK AFTER IRRADIATION | ABSORBANCE OF SALINE FOURTH WEEK AFTER IRRADIATION |
|---|---|---|---|---|---|---|---|
| #1 | 0 WEEKS | #1 - 9.235% | #1 - 2.38 MRad | 70° - .024 | 70° - .039 | 70° - .043 | 70° - .045 |
| #2 | | #2 - 8.226% | #2 - 2.78 MRad | 100° - .047 | 100° - .050 | 100° - .043 | 100° - .065 |
| | | | | 150° - .122 | 150° - .125 | 150° - .149 | 150° - .161 |
| #3 | 1 WEEK | #3 - 7.902% | #3 - 2.45 MRad | 70° - .029 | 70° - .043 | 70° - .046 | 70° - .040 |
| #4 | | #4 - 8.827% | #4 - 2.69 MRad | 100° - .049 | 100° - .047 | 100° - .063 | 100° - .040 |
| | | | | 150° - .148 | 150° - .130 | 150° - .159 | 150° - .089 |
| #5 | 2 WEEKS | #5 - 9.24% | #5 - 2.02 MRad | 70° - .038 | 70° - .038 | 70° - .030 | 70° - .028 |
| #6 | | #6 - 8.74% | #6 - 2.02 MRad | 100° - .033 | 100° - .048 | 100° - .031 | 100° - .030 |
| | | | | 150° - .115 | 150° - .142 | 150° - .075 | 150° - .086 |

TABLE I-continued

| BOX NO. | TIME ELAPSED BETWEEN CONDITIONING OF SPONGES & STERILIZATION BY IRRADIATION | MOISTURE CONTENT AT TIME OF IRRADIATION | DOSE LEVEL OF IRRADIATION | ABSORBANCE OF SALINE FIRST WEEK AFTER IRRADIATION | ABSORBANCE OF SALINE SECOND WEEK OF IRRADIATION | ABSORBANCE OF SALINE THIRD WEEK AFTER IRRADIATION | ABSORBANCE OF SALINE FOURTH WEEK AFTER IRRADIATION |
|---|---|---|---|---|---|---|---|
| #7 | 4 WEEKS | 8.13% | 2.96 MRad | 70° - .031<br>100° - .032<br>150° - .077 | 70° - .022<br>100° - .026<br>150° - .083 | 70° - .027<br>100° - .031<br>150° - .090 | |
| #8 | N/A | N/A | NONE | 70° - .017<br>100° - .013<br>150° - .050 | | | 70° - .016<br>100° - .027<br>150° - .041 |

As illustrated by the absorbance measurements in Table 1, the feasibility of substantially reducing discoloration in commercial laparotomy sponges by controlling their water content is not adversely affected by time delays between their packaging, irradiation and exposure to elevated temperatures. In fact, some of the absorbance measurements at 150° F. indicate that a time delay between conditioning the sponges between 6% and 10% water content by weight and irradiating the sponges might reduce the discoloration of the sponges.

Possible further improvement in the reduction of sponge discoloration is considered to have limited practical value since (1) even without a time delay between conditioning and irradiation of the sponges the absorbance at the highest tested temperature, i.e., 150° F., is virtually undetectable to the human eye (i.e., below 0.15 units) and (2) exposure of the sponges to temperatures above 150° F. during storage and transportation are very unlikely. Accordingly, any discoloration improvement resulting from a delay between the conditioning of the sponges and their irradiation—as suggested by the limited data in Table 1—was not verified by further and more extensive experiments.

It is, however, hypothesized that the time delays between conditioning and sterilization of the sponges may have allowed the water content of the sponges to equilibrate throughout the cellulosic material. Therefore, the cellulosic material of the sponges becomes more fully hydrated with water. It is believed that allowing time for the water to equilibrate and the cellulosic material to fully hydrate before the material is irradiated will result in maximum color stability for irradiation-sterilized cellulosic material.

From the foregoing, it will be appreciated that water or moisture preconditioning of cellulosic material shows remarkable success in stabilizing the color of the material when it is subjected to post-sterilization heating. In addition, by providing a water content of at least 8% by weight, the cellulosic material will resist discoloration at the most extreme temperatures likely to be encountered during storage and transportation. By limiting the water content to 12% or less by weight, the cellulosic material will remain dry to the touch. Also it will be appreciated that the addition of moisture or water to cellulosic material in accordance with the invention is safe, inexpensive and nontoxic.

We claim:

1. A process for sterilizing cellulosic material which is subject to possible subsequent exposure to undue thermal conditions, said process comprising the steps of:
    prehumidifying said cellulosic material to a moisture content not less than 6.5% by weight which is sufficient to prevent discoloration of said cellulosic material during a subsquent irradiation step and further sufficient to prevent discoloration of said cellulosic material upon possible thermal conditions after irradiation;
    sealing said cellulosic material from ambient conditions so as to maintain said cellulosic material at said moisture content; and
    irradiating said cellulosic material with a sufficient radiation dosage to cause biological death.

2. A process as set forth in claim 1 wherein said cellulosic material is sealed in a package having low vapor permeability.

3. A process as set forth in claim 1 wherein the cellulosic material is prehumidified to a moisture content which leaves the material dry to the touch after the material has been irradiated.

4. A process for sterilizing cellulosic material as set forth in claim 3 wherein the material is prehumidified to a water content within the range from about 8% to about 10% by weight.

5. A process as set forth in claim 1 wherein the cellulosic material is prehumidified by exposure to air at predetermined temperature and relative humidity.

6. A process as set forth in claim 5 wherein the cellulosic material is cotton which is prehumidified by exposure to air at 70° F.±2 and at 80%±5% relative humidity for a time period sufficient to stabilize the moisture content of the cotton at not less than 6.5% by weight.

7. A sterilized cellulosic material capable of resisting discoloration caused by possible subsequent exposure to undue post-sterilization thermal conditions, said material being made by a process comprising:
    prehumidifying said cellulosic material to a moisture content not less than 6.5% by weight which is sufficient to prevent discoloration of said cellulosic material during a subsequent irradiation step and further sufficient to prevent discoloration of said cellulosic material upon possible thermal conditions after irradiation;
    sealing said cellulosic material in a package having a low vapor permeability so as to maintain said prehumidified cellulosic material at a moisture content of not less than 6.5% by weight; and
    irradiating the prehumidified cellulosic material with a sufficient radiation dosage to cause biological death.

8. A sterilized cellulosic material as set forth in claim 7 wherein the material is prehumidified to a water content which leaves the material dry to the touch after the material has been irradiated.

9. A sterilized cellulosic material as set forth in claim 8 wherein the material is prehumidified to a water content within the range from about 8% to about 10% by weight.

10. A sterilized cellulosic material as set forth in claim 7 wherein the material is prehumidified to a water content sufficient to prevent visually perceivable discoloration resulting from possible subsequent exposure of the material to post-irradiation temperatures up to and including 150° F.

11. A sterilized cellulosic material as set forth in claim 10 wherein the material is prehumidified to a water content which leaves the material dry to the touch after the material has been irradiated.

12. A radiation-sterilized, cellulosic material capable of resisting discoloration upon possible subsequent exposure to undue post-sterilization thermal heating, said material resulting from a process comprising the steps of:
  prehumidifying said cellulosic material to a predetermined moisture content based upon the weight of the cellulosic material with said moisture content being of a value not less than 6.5% which prevents visually noticeable discoloration of said radiation-sterilized, cellulosic material upon possible subsequent post-sterilization exposure to temperatures up to about 150° F.;
  sealing said cellulosic material in a package having a low vapor permeability so as to maintain said prehumidified cellulosic material approximately at said predetermined moisture content by weight; and
  irradiating the prehumidified cellulosic material with a sufficient radiation dosage to cause biological death.

13. A radiation-sterilized, cellulosic material as set forth in claim 12 wherein the material is prehumidified to a water content within the range from about 8% to about 10% by weight.

* * * * *